United States Patent
Soeda

(10) Patent No.: US 7,342,226 B2
(45) Date of Patent: Mar. 11, 2008

(54) STRESS MEASURING METHOD AND SYSTEM

(75) Inventor: Takeshi Soeda, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 11/349,131

(22) Filed: Feb. 8, 2006

(65) Prior Publication Data
US 2007/0069128 A1 Mar. 29, 2007

(30) Foreign Application Priority Data
Sep. 28, 2005 (JP) ............................. 2005-281993

(51) Int. Cl.
*G01N 23/00* (2006.01)

(52) U.S. Cl. ................. 250/311; 250/311; 250/306; 250/307; 250/310

(58) Field of Classification Search ................ 250/311, 250/310, 307, 306
See application file for complete search history.

(56) References Cited

U.S. PATENT DOCUMENTS 6,750,451 B2 * 6/2004 Koguchi et al. ............ 250/311
6,844,551 B2 * 1/2005 Takeno ...................... 250/311
2005/0061974 A1 * 3/2005 Kim et al. .................. 250/310

FOREIGN PATENT DOCUMENTS

| JP | 6-36729 | 2/1994 |
| JP | 7-169811 | 7/1995 |
| JP | 2000-9664 | 1/2000 |
| JP | 2004-77247 | 3/2004 |

* cited by examiner

*Primary Examiner*—Jack I. Berman
*Assistant Examiner*—Andrew Smyth
(74) *Attorney, Agent, or Firm*—Kratz, Quintos & Hanson, LLP

(57) ABSTRACT

A convergent electron beam is incident on an evaluation region of a crystalline material to obtain a HOLZ pattern formed by the convergent electron beam transmitted to the crystalline material (Steps S11 to S13), a split width of the HOLZ line of the obtained HOLZ pattern is computed (Step S14), and a stress in the evaluation region of the crystalline material is evaluated based on the split width of the HOLZ line (Step S15). Thus, the stress measuring method and system can measure with good precision a local lattice strain amount and stress value of the crystalline material, and a stress value of a stress source applying a stress to the crystalline material.

14 Claims, 20 Drawing Sheets

TRANSMISSION IMAGE    DIFFRACTION IMAGE t=55nm t=164nm t=273nm t=381nm t=490nm t=600nm

DISTANCE FROM INTERFACE BETWEEN CONTACT
MATERIAL AND SILICON SUBSTRATE

THICKNESS : 250nm

THICKNESS : 275nm

STRESS MEASURING METHOD AND SYSTEM

CROSS-REFERENCE TO RELATED APPLICATIONS

This application is based upon and claims the benefit of priority from the prior Japanese Patent Application No. 2005-281993, filed on Sep. 28, 2005, the entire contents of which are incorporated herein by reference.

BACKGROUND OF THE INVENTION

The present invention relate to a stress measuring method and system, more specifically, a stress measuring method and system for measuring a lattice strain amount and a stress value in an infinitesimal region by convergent-beam electron diffraction method.

It is known that when a stress is applied to a crystalline material from the outside, lattice strains takes place and influence various properties of the crystalline material. Especially, lattice strains accompanying high integration and downsizing of semiconductor devices is an important factor for deciding the device characteristics of the electronic devices. On the other hand, lattice strains generated in crystalline materials are positively utilized to thereby improve or suppress the degradation of the electronic characteristics of electronic devices. Accordingly, to design required devices, it is important to measure stresses, which are a cause for the lattice strains of the crystalline materials forming electronic devices.

A lattice strain, which can be grasped as a change rate of a lattice constant, has been measured by lattice constant measuring methods, such as x-ray diffraction method, Raman analysis, convergent-beam electron diffraction method, etc. Among them, the convergent-beam electron diffraction method, which can decide the lattice constant with space resolving power of the nanometer-order, is used in measuring the lattice strain of small electronic devices.

The convergent-beam electron diffraction method is described in, e.g., Reference 1 (Japanese published unexamined patent application No. Hei 06-036729), Reference 2 (Japanese published unexamined patent application No. Hei 07-169811), Reference 3 (Japanese published unexamined patent application No. 2000-009664) and Reference 4 (Japanese published unexamined patent application No. 2004-077247).

SUMMARY OF THE INVENTION

The convergent-beam electron diffraction method uses geometric changes of HOLZ (High Order Laue Zone) patterns given by applying convergent electron beam to a crystalline material. The HOLZ lines forming a HOLZ pattern are shifted in accordance with a lattice strain, and shift amount of the HOLZ lines is measured to thereby compute a strain amount of the lattice.

The detection precision of the strain amount depends on the visibility of the HOLZ lines. When a lattice is uniformly strained, clear HOLZ lines can be given, and the detection precision can be high. In practical samples, however, all lattice strains are not uniform, and clear patterns are not always ensured. For example, around a transistor of a semiconductor device, a number of stressors (stress sources), such as plugs, interconnections, device isolation film, etc., are arranged at various positions near the device region, and strained sites are disuniform depending on the regions. In this case, the HOLZ lines are not clear and furthermore are split. In this state, positions of the HOLZ lines cannot be identified, and accurate measurement of the lattice strains cannot be made.

An object of the present invention is to provide a stress measuring method and system which can measure with good precision a local lattice strain amount and stress value of a crystalline material, and a stress value of a stress source applying stresses to the crystalline material.

According to one aspect of the present invention, there is provided a stress measuring method comprising: applying a convergent electron beam to an evaluation region of a crystalline material and obtaining a HOLZ pattern as a transmitted image of the convergent electron beam; measuring a split width of a HOLZ line of the HOLZ pattern; and evaluating a stress in the evaluation region of the crystalline material, based on the split width of the HOLZ line.

According to another aspect of the present invention, there is provided a stress measuring system comprising: an electron microscope for applying a convergent electron beam to an evaluation region of a crystalline material and obtaining a HOLZ pattern given as a transmission image of the convergent electron beam; and a processing device for measuring a split width of a HOLZ line of the HOLZ pattern obtained by the electron microscope and evaluating a stress in the evaluation region of the crystalline material, based on the split width of the HOLZ line.

According to the present invention, convergent electron beam is applied to an evaluation region of a crystalline material to be measured, a HOLZ pattern formed by the convergent electron beam transmitted to the crystalline material is obtained, a split width of the HOLZ line of the HOLZ pattern is measured, local stress of the crystalline material is evaluated based on the measured spit width of the HOLZ line, whereby a stress and a lattice strain in a disuniformly strained site of a much infinitesimal region can be precisely measured.

DETAILED DESCRIPTION OF THE PREFERRED EMBODIMENTS

A First Embodiment

The stress measuring method and system according to a first embodiment of the present invention will be explained with reference to FIGS. 1 to 11.

Figure 1A:
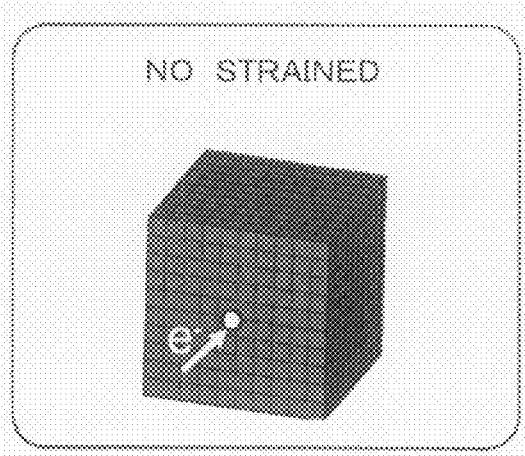
FIG. 1 is a diagrammatic view showing the stress measuring system according to a first embodiment of the present invention.
Figure 1B:
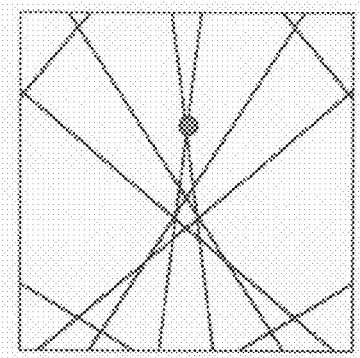
Figure 2A:
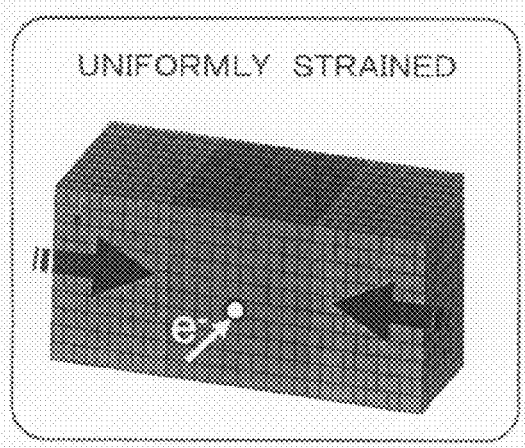
FIG. 2 is a diagrammatic view showing the method for measuring a sample by STEM method.
Figure 2B:
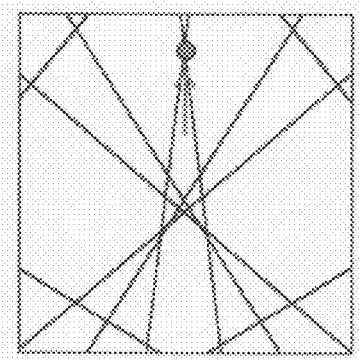
Figure 3A:
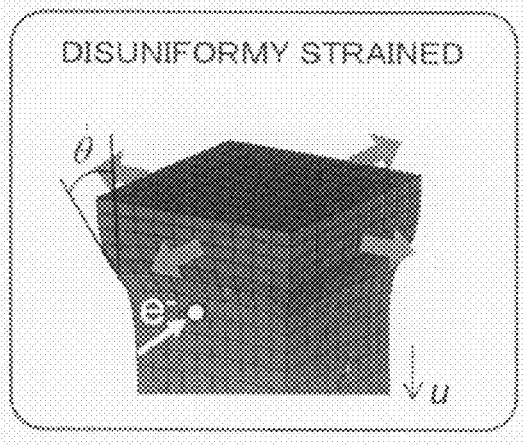
FIG. 3 is a view showing a convergent-beam electron diffraction image given when convergent electron beam is incident along the zone axis.
Figure 3B:
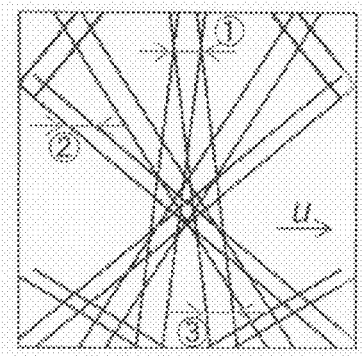
Figure 2:
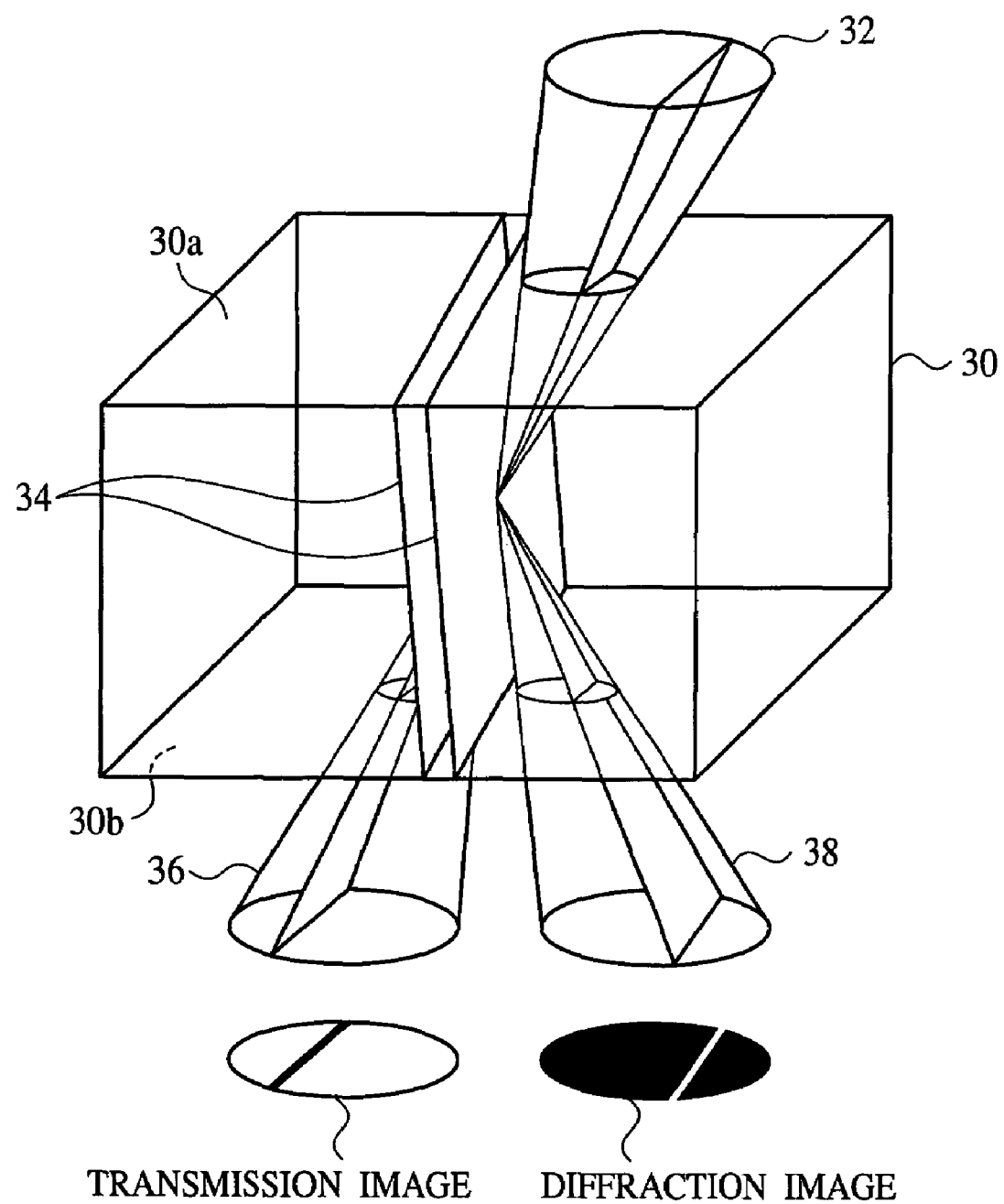
Figure 3:
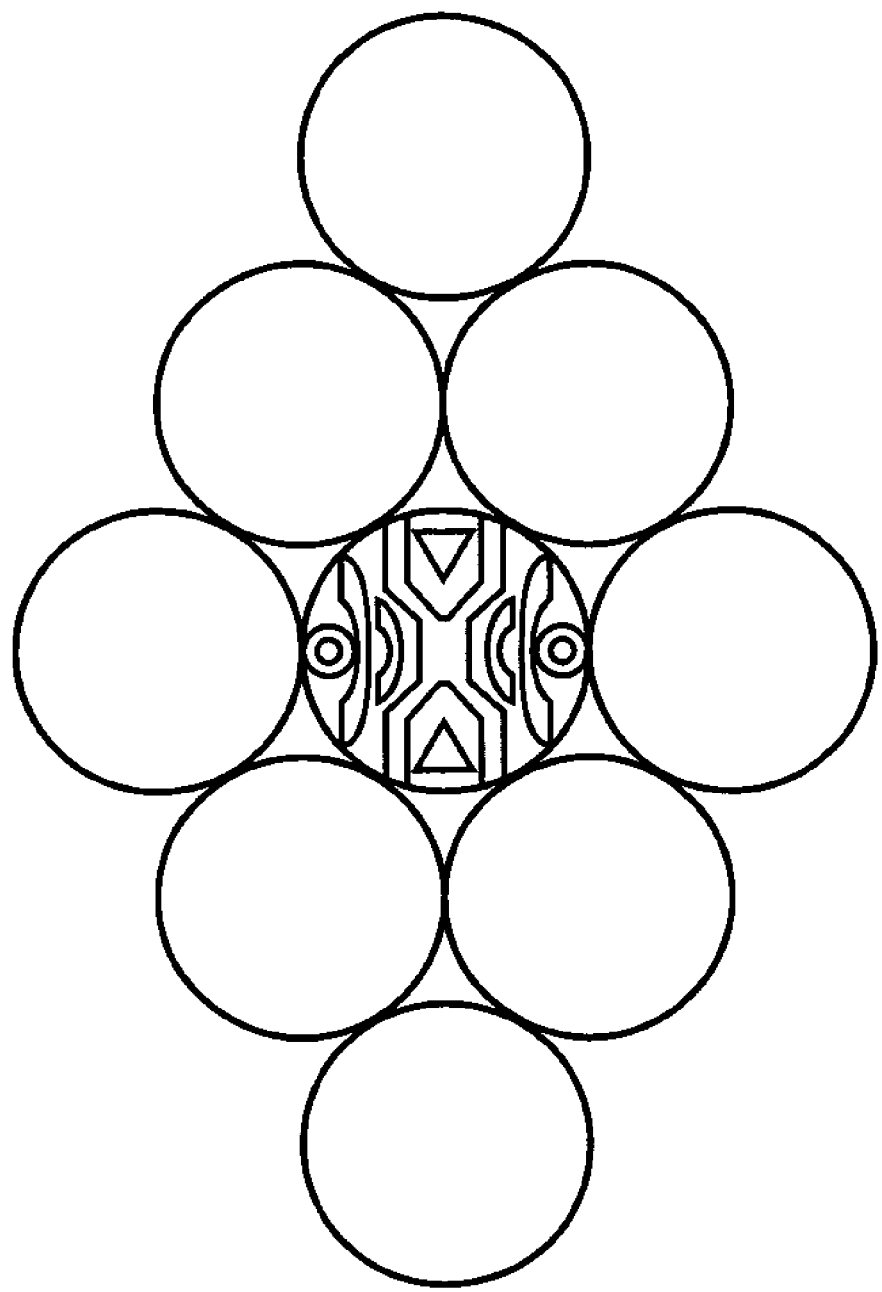
Figure 4:
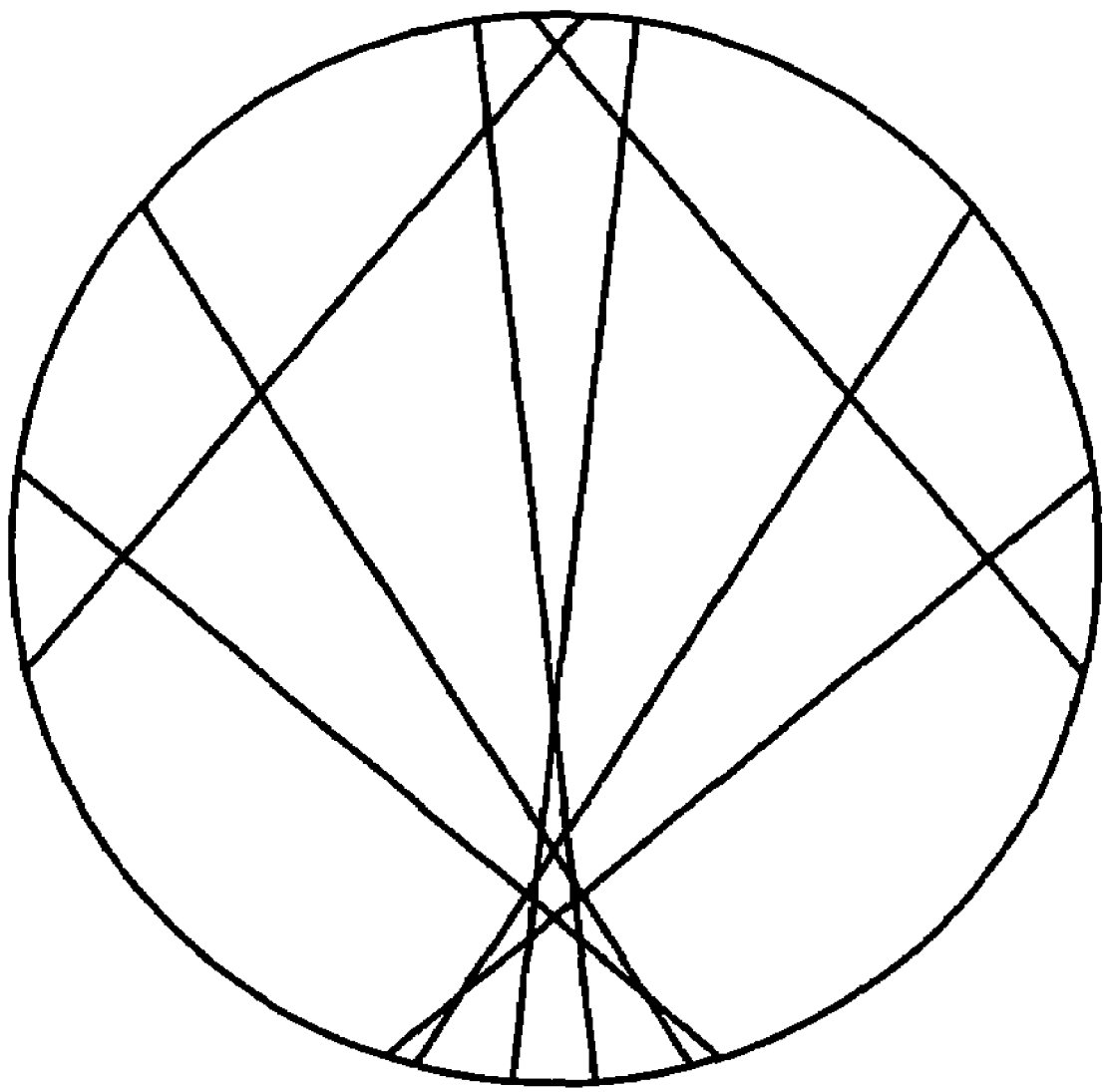
FIG. 4 is a view showing a HOLZ pattern of a uniformly strained sample.
Figure 5:
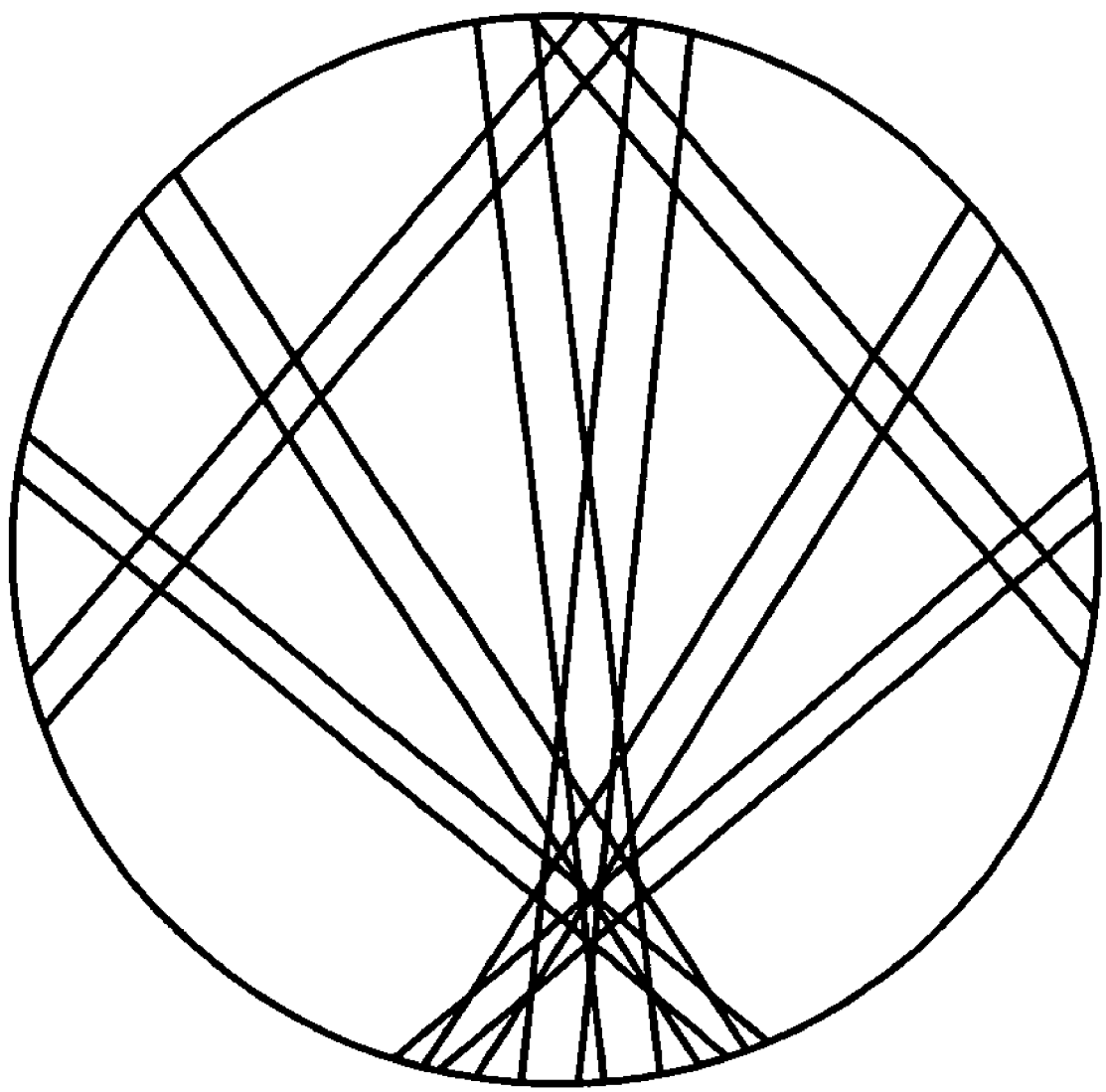
FIG. 5 is a view showing a HOLZ pattern of a disuniformly strained sample.
Figure 6:
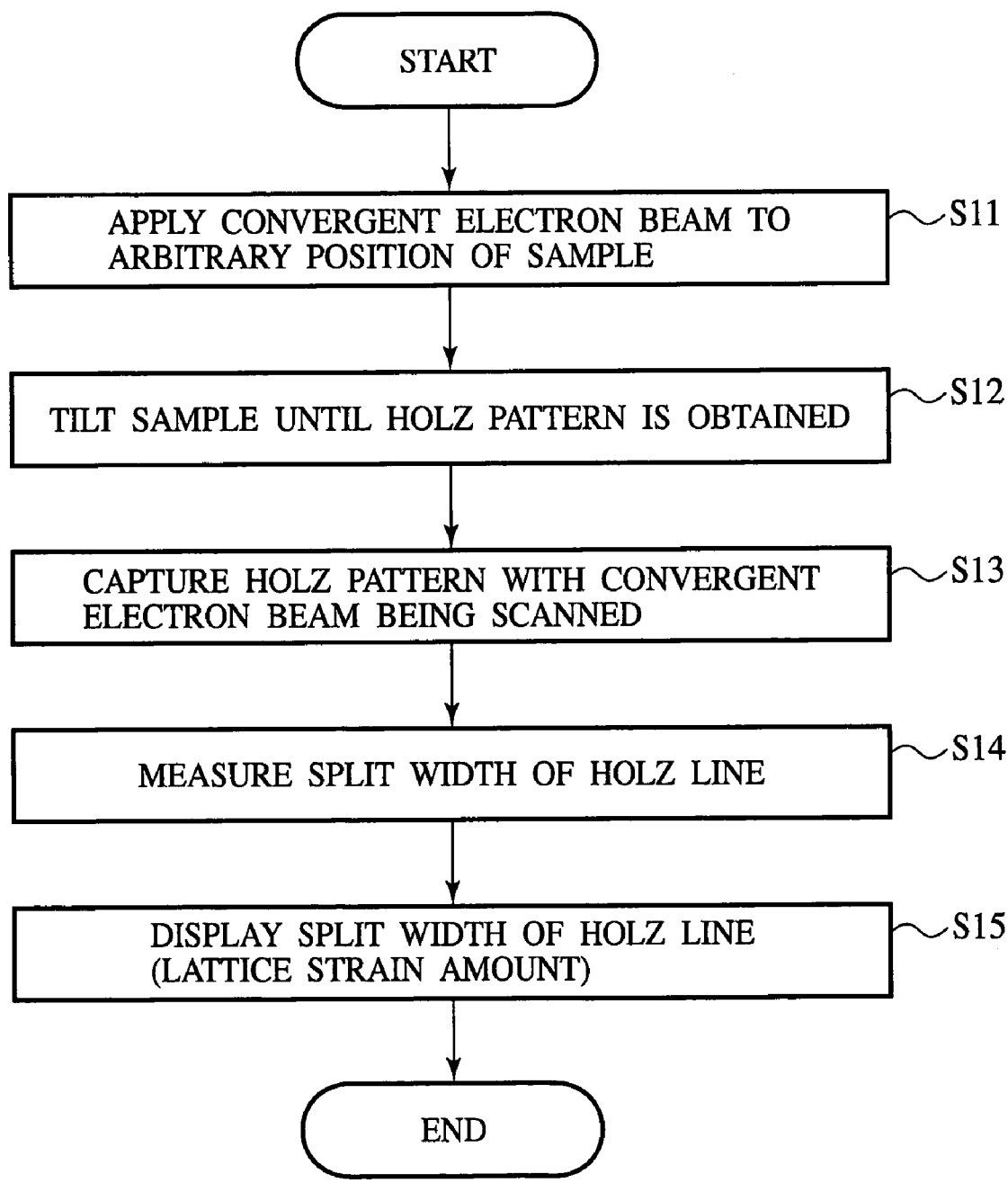
FIG. 6 is a flow chart of the stress measuring method according to a first embodiment of the present invention.
Figure 7:
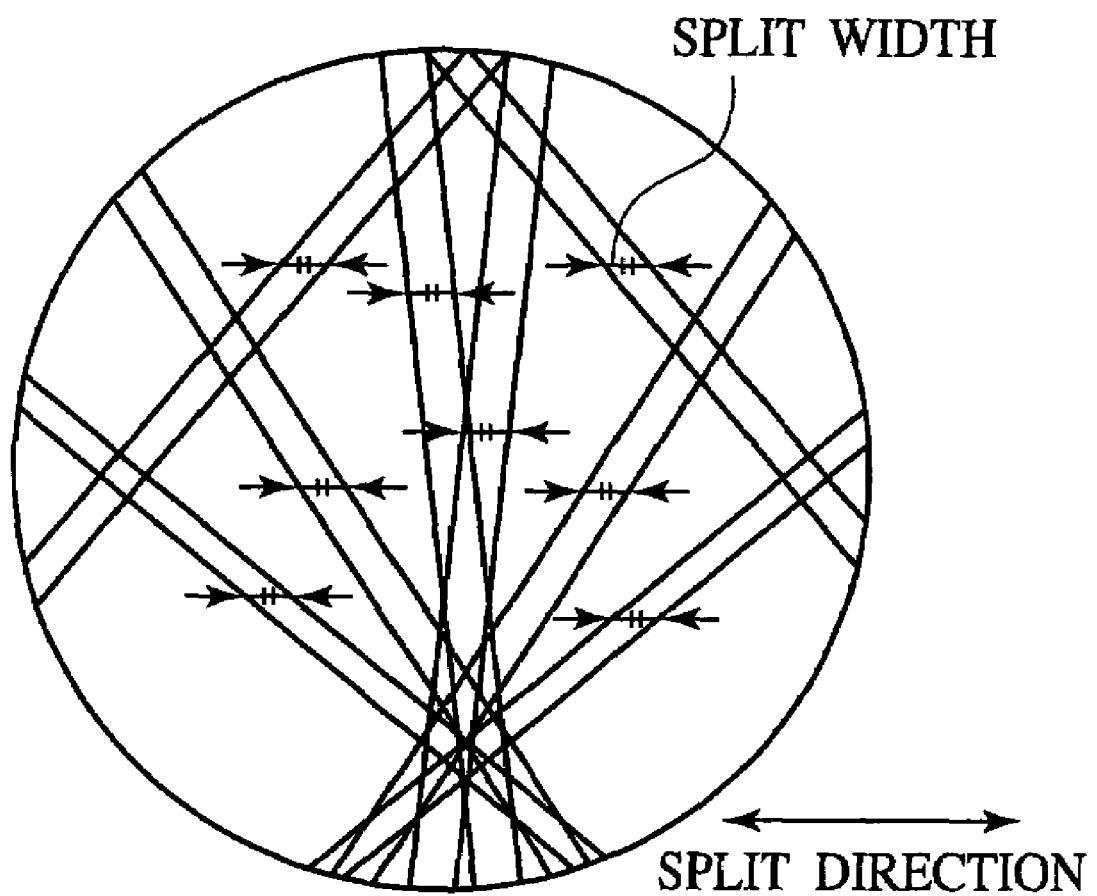
FIG. 7 is a view explaining the split width and split direction of the HOLZ lines.
Figure 8:
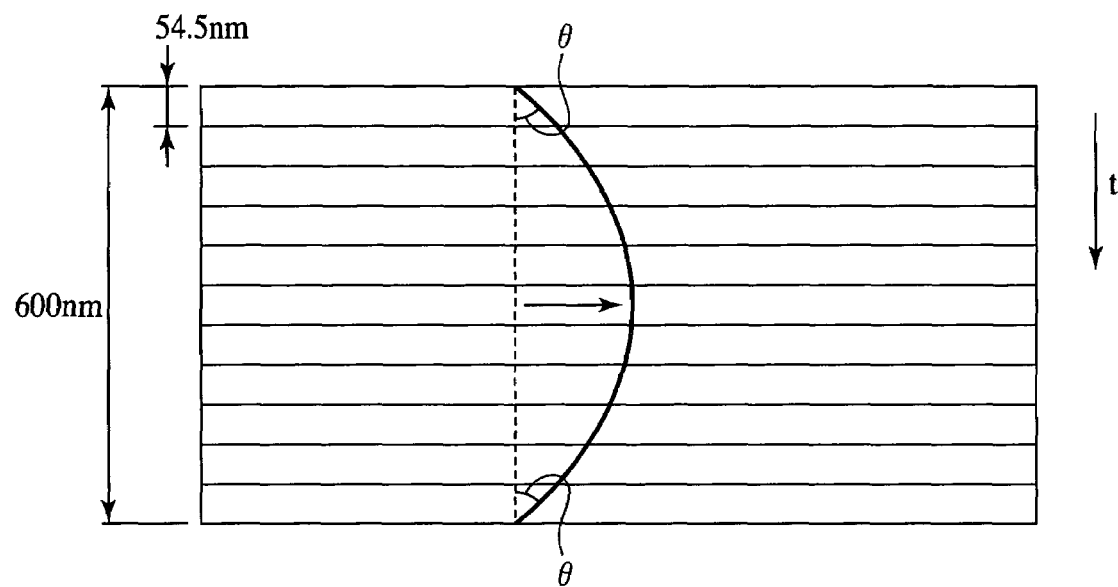
FIG. 8 is a diagrammatic view of the model used in computing the relationship between the lattice bending amount of the sample and the split width of the HOLZ line.
Figure 10:
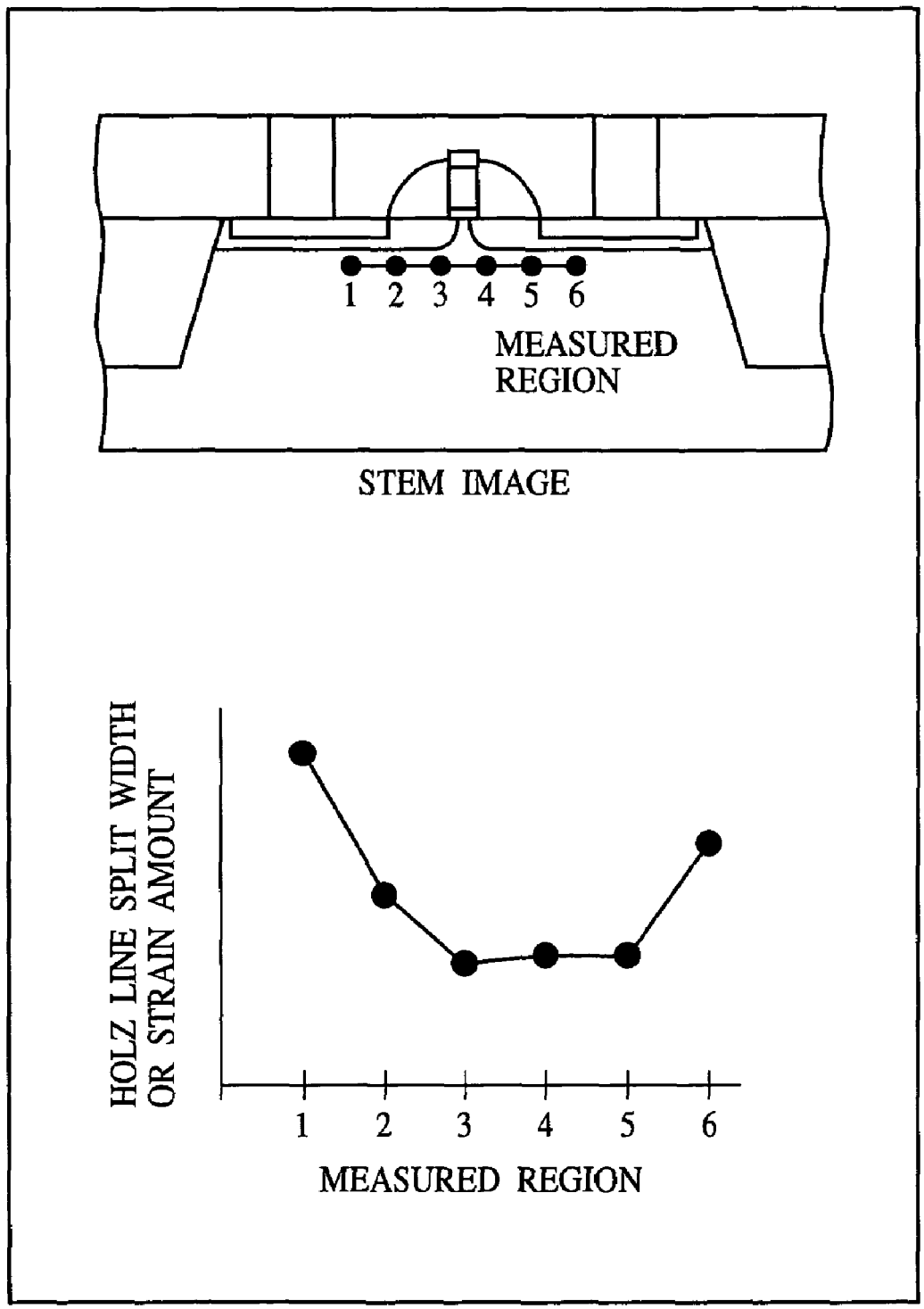
FIGS. 10 and 11 are views showing examples of the display of the result of the measurement by the stress measuring method according to the first embodiment of the present invention.
Figure 11:
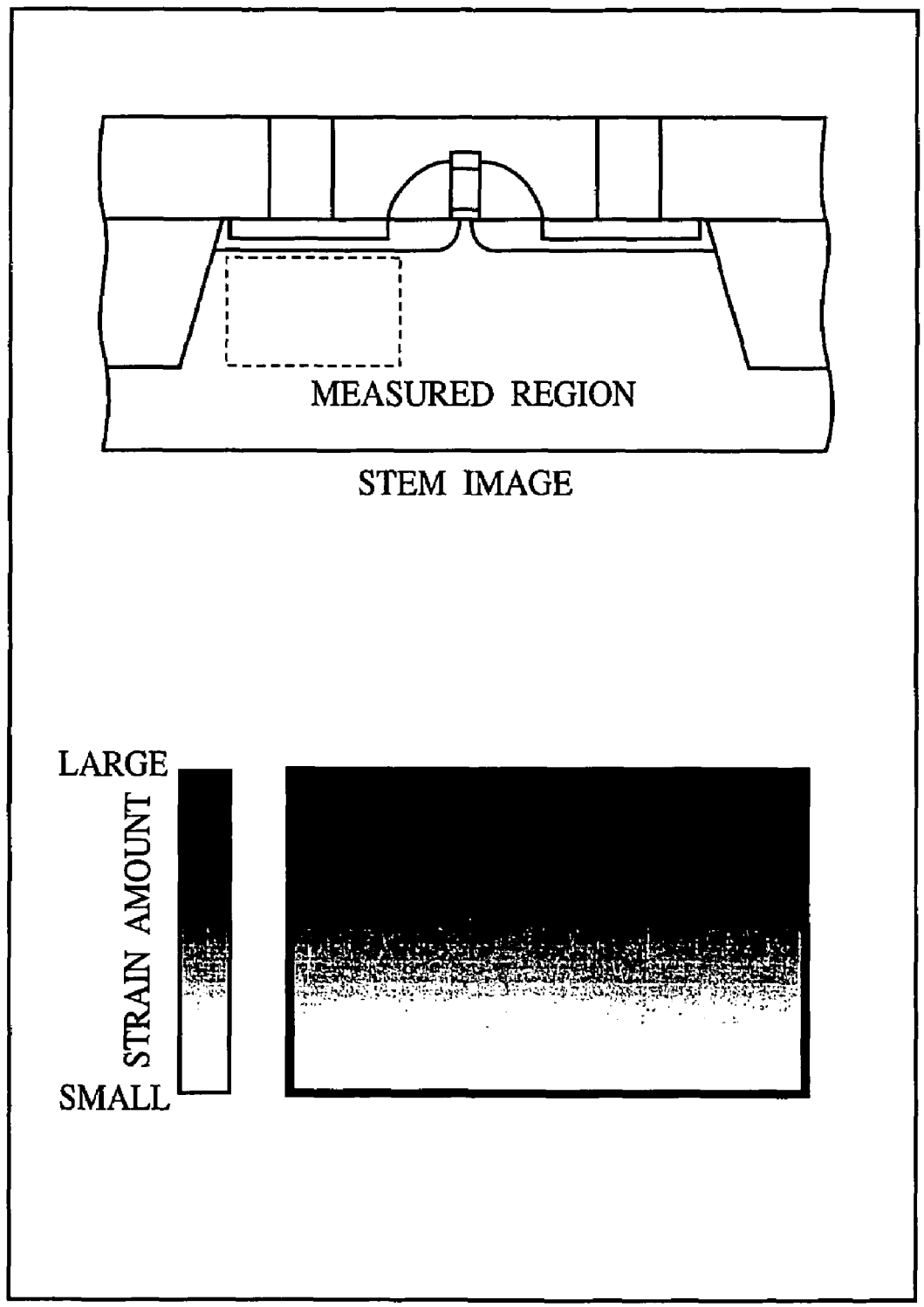
Figure 1:
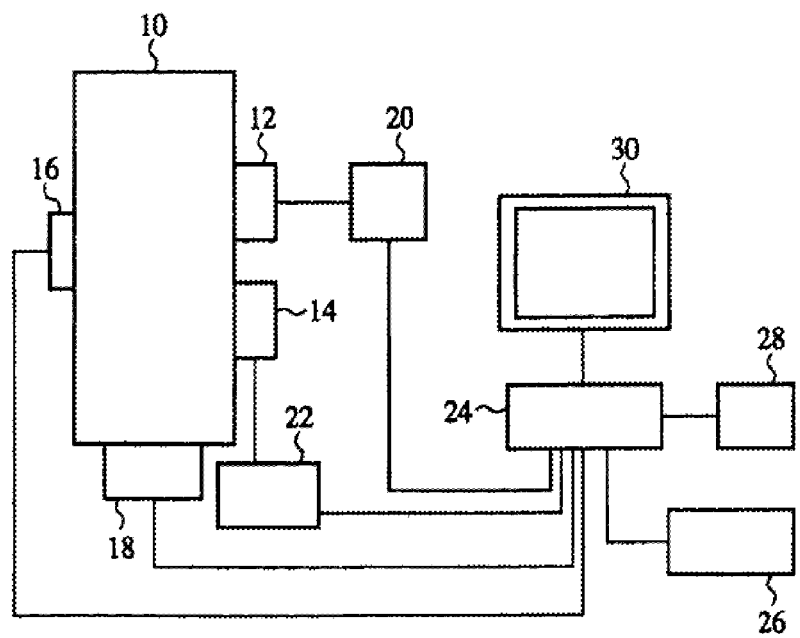

FIG. 1 is a diagrammatic view showing the stress measuring system according to the present embodiment. FIG. 2 is a diagrammatic view showing the method for measuring a sample by STEM method. FIG. 3 is a view showing a convergent-beam electron diffraction image given when convergent electron beam is incident along the zone axis. FIG. 4 is a view showing a HOLZ pattern of a uniformly strained sample. FIG. 5 is a view showing a HOLZ pattern of a disuniformly strained sample. FIG. 6 is a flow chart of the stress measuring method according to the present embodiment. FIG. 7 is a view explaining the split width and split direction of the HOLZ lines. FIG. 8 is a diagrammatic view of the model used in computing the relationship between the lattice bending amount of the sample and the split width of the HOLZ line. FIGS. 9A-9F are views showing the relationship between the lattice bending amount of the sample and split width of the HOLZ line. FIGS. 10 and 11 are views showing examples of the display of the result of the measurement.

First, the stress measuring system according to the present embodiment will be explained with reference to FIG. 1.

The stress measuring system according to the present embodiment includes an STEM (Scanning Transmission Electron Microscope) 10. The STEM 10 includes a scanning lens system control device 12 which controls the scanning lens system for controlling an electron beam to be applied to a sample, a transmission lens system control device 14 which controls the transmission lens system for controlling the electron beam transmitted to the sample, a sample control device 16 for controlling a position and an angle of the sample to the electron beam, and an image capturing device 18 which captures a pattern (transmitted electron pattern) of the electron beam transmitted to the sample.

The sample control device 16 is connected to a processing device 24. The scanning lens system control device 12 is connected to the processing device 24 via a scanning lens system control input device 20. The transmission lens system control device 14 is connected to the processing device 24 via a transmission lens system control input device 22. Thus, the electron beam is converged and applied to an arbitrary position on a sample at an arbitrary angle, and the transmitted electron beam is led to the image capturing device 18.

The processing device 24 functions as the control device which controls the scanning lens system control device 12, the transmission lens system control device 14, the sample control device 16, etc. and also as the analysis device for analyzing measured data inputted by the image capturing device 18. An input device 26 which inputs from the outside information necessary for the measurements, etc., an outside memory device 28 which stores database, etc. to be used for the analysis of the measured data, and display device 30 which displays the analysis results, etc. are connected to the processing device 24.

Then, STEM method (Scanning Transmission Electron Microscopy) used in the stress measuring method according to the present invention will be summarized with reference to FIGS. 2 to 5. In the STEM method, convergent electron beam is incident on a sample and scanned, and electron diffraction intensities and electron scattering intensities at the respective incidence points are read by a detector to visualize. By using the STEM method, magnified images (STEM images) of various structures, typically semiconductor devices can be obtained.

As shown in FIG. 2, a convergent electron beam 32 is applied to a front. surface 30*a* of a sample 30 to be measured. The applied electron beam passes through the sample 30 and exits at a back surface 30*b* of the sample 30.

When the convergent electron beam 32 is incident along the zone axis direction, such as <110>, <100> or others, where the atoms are orderly arranged, the pattern of the transmitted electron beam 36 as shown in FIG. 3 is given. This pattern is given by the interference of the electron waves. In structures, such as semiconductor devices, in which, in many cases, the devices are formed along the zone axis, and samples cut out along the device structure give such pattern.

The incident direction of the convergent electron beam 32 is tilted from the zone axis by several degrees to thereby weaken the interference of the electron beams. At this time, when the relationship between the wavelength of the electron beam and the space between the lattice planes 34 satisfies the Bragg reflection condition, those of the incident convergent electron beam 32, which have been incident at a prescribed angle to the lattice planes 34 satisfying the Bragg reflection condition are diffracted, and prescribed diffracted electron beam 38 can be obtained.

The diffracted electron beam 38 form a straight line (High Order Laue Zone line, hereinafter called HOLZ line) extended in a direction associated with the plane orientation of the lattice planes 34. The transmitted electron beam 36 is those of the convergent electron beam 32 incident on the sample 30, which have not been diffracted, and the transmitted pattern formed by the transmitted electron beam 36 also has HOLZ line.

Strained regions introduced into a crystalline material can be classified in a closed system and an open system in terms of structure. The former is a region closed by stressors, and the latter is a region which is not closed by the stressors. Near the device region of a MOSFET, for example, the relationship between the device isolation region and the device region can be considered to be the closed system, and the relationship between the contact material or the plug material, and the device region is the open system.

In the closed system, where generally stressors enclose an evaluation region, the crystal lattice in the evaluation region is uniformly strained. In such case, the strain amount of the crystal strain can be measured by the usual convergent-beam electron diffraction method (e.g., refer to Reference 4). When such sample is locally observed, the HOLZ pattern as shown in FIG. 4 can be given.

In contrast to this, in the open system, where stressors are singly present, when the evaluation region is locally observed, the crystal lattice in the evaluation region is disuniformly strained. In such case, when sample is cut out, the stresses applied to the evaluation region cannot be sustained and are released, and the crystal lattice is bent. When the bent samples are locally observed, the split HOLZ pattern as shown in FIG. 5 is given.

Next, the stress measuring method according to the present embodiment will be specified with reference to FIG. 6.

FIG. 6 is a flow chart showing the stress measuring method according to the present embodiment. In this flow chart, a HOLZ pattern of an evaluation region is measured (Steps S11-S13), a split width of the HOLZ line is measured (Step S14), and the split width of the HOLZ line is displayed (Step S15).

First, a sample to be measured is placed on a stage in the STEM 10, and the inside of the STEM 10 is depressurized to a prescribed pressure. The sample to be measured is in advance formed in a thin piece which transmits the electron beam.

Next, a convergent electron beam is applied to the sample, and the scanning lens system control device 12 is controlled via the scanning lens system control input device 20 to stop the electron beam at an arbitrary position on the sample (Step S11). The convergent electron beam can be converged into a very small beam diameter of about several nanometers and can enter into much infinitesimal region of the sample. The incident position of the electron beam can be confirmed by the STEM image.

Next, the sample is tilted to the convergent electron beam by the sample control device 16 to thereby form a HOLZ pattern by the transmitted electron beam (Step S12).

Next, with the convergent electron beam being scanned by the scanning lens system control device 12, patterns are imaged, and a HOLZ pattern at the arbitrary position on the sample is given (Step S13).

To obtaining the HOLZ pattern by the STEM 10, imaging device, such as a CCD camera or others, is used as the image capturing device 18. The scanning rate and the shutter speed are synchronized, whereby the HOLZ patterns at the respective incident points can be continuously captured. At this time, the position of the electron beam is controlled by the scanning lens system control device 12, whereby HOLZ pattern can be captured respectively at an arbitrary incident point in the zero-dimensional scanning, incident points on a line in the one-dimensional scanning, and at incident points in plane in the two-dimensional scanning.

Objects to be measured by the stress measuring method according to the present invention are samples whose crystal lattices are strained asymmetrically, and the HOLZ lines are split in straight lines in parallel with each other (see FIG. 5).

Then, based on the HOLZ patterns given by imaging the sample at respective points, the split widths of the HOLZ lines are measured (Step S14).

The split width of the HOLZ line is an interval of a HOLZ line split by the bending of the sample (split HOLZ line), which is measured in a split direction of the HOLZ lines. The split direction of the HOLZ line is one direction determined for each HOLZ pattern and a direction where intervals of all the split HOLZ lines are equal (see FIG. 7).

Here, the relationship between the bending amount of the sample and the split width of the HOLZ lines will be explained with reference to FIGS. 8-9F.

As a sample to be measured, a model as shown in FIG. 8 is assumed. The sample shown in FIG. 8 has a 600 nm-thickness and, for the convenience of the explanation, has regions of 11 slices of the same depth-wise thickness. One slice has an about 54.5 nm-thickness.

It is assumed that in the sample shown in FIG. 8, the crystal plane which should be naturally parallel to the thickness-wise (as shown by the dotted line in the drawing) are bent as shown by the solid line in the drawing. The lattice bending amount at this time is expressed by a difference (e.g., $2\theta$) between a crystal orientation near the front surface of the sample (e.g., the first slice) and a crystal orientation near the back surface of the sample (e.g., the $11^{th}$ slice). In the following description, it is assumed that the angle $\theta$ is 1.53 [mrad].

Figure 9A:
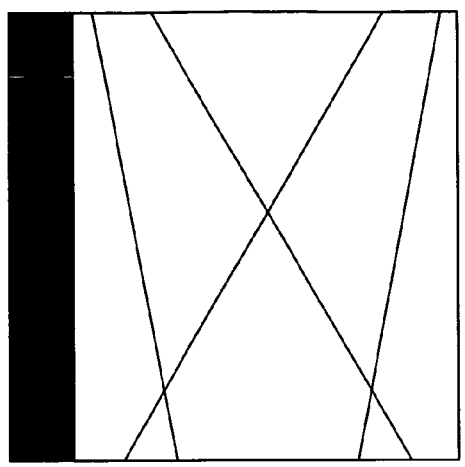
FIGS. 9A-9F are views showing the relationship between the lattice bending amount of the sample and split width of the HOLZ line.
Figure 9B:
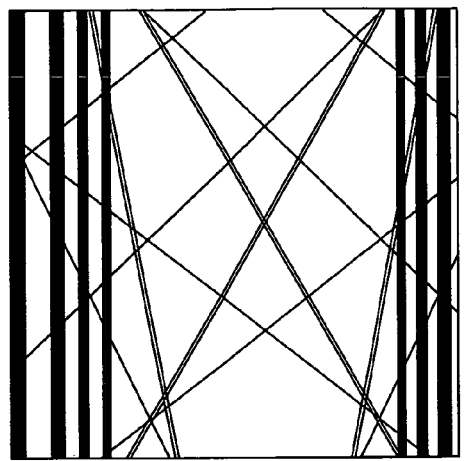
Figure 9C:
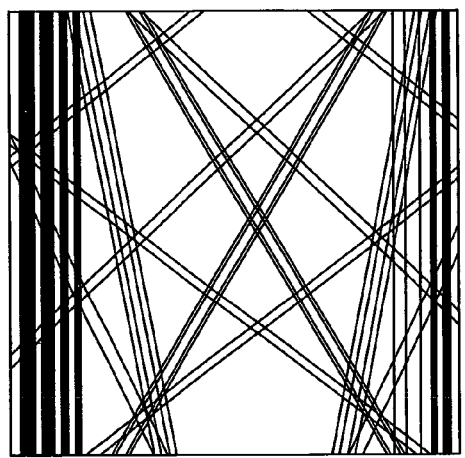
Figure 9D:
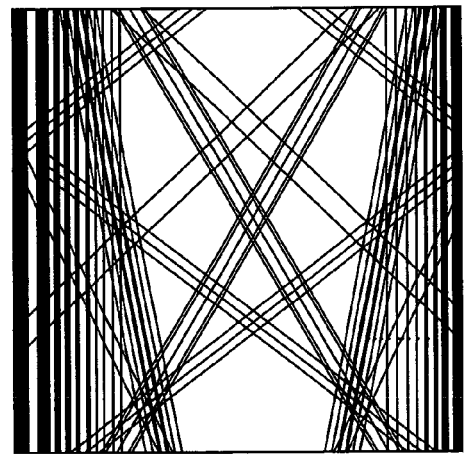
Figure 9E:
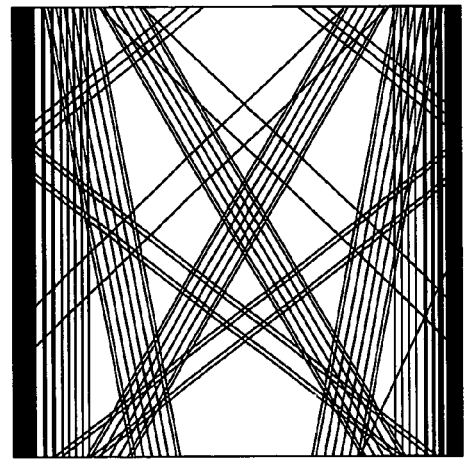
Figure 9F:
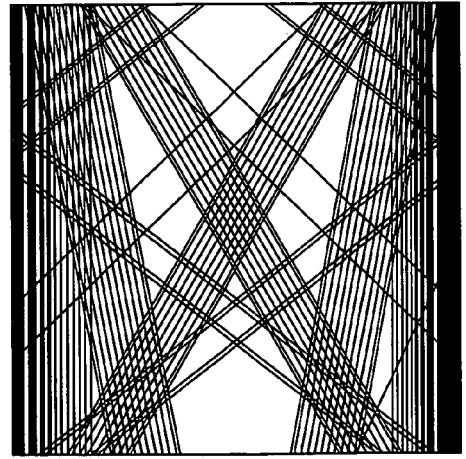

FIGS. 9A-9F are views of HOLZ patterns given by simulation with the thickness of the sample of FIG. 8 increased in the unit of slices. In FIG. 9A, the sample is formed of one slice on the front surface side (thickness: 55 nm). In FIG. 9B, the sample is formed of three slices on the front surface side (thickness: 164 nm). In FIG. 9C, the sample is formed of five slices on the front surface side (thickness: 273 nm). In FIG. 9D, the sample is formed of seven slices on the front surface side (thickness: 381 nm). In FIG. 9E, the sample is formed of nine slices on the front surface side (thickness: 490 nm). In FIG. 9F, the sample is formed of eleven slices (600 nm). The lattice bending amount is expressed by an amount of a difference between a crystal orientation near the front surface of the sample and a crystal orientation near the back surface of the sample. Accordingly, as in the examples of FIGS. 9A to 9B, the lattice bending amount is larger as the sample is thicker.

As shown in FIGS. 9A-9F, the split width of the HOLZ line increases as the lattice bending amount of the sample is larger. That is, the split width of the HOLZ line has the correlation with the lattice strain amount, and the split width of the HOLZ line is measured, whereby the lattice strain of the sample to be evaluated can be qualitatively given.

Next, the split width of the HOLZ line measured in the above-described steps is displayed on the display device 30 (Step S15).

When the HOLZ patterns are captured in Step S13, the HOLZ patterns are stored in the outside memory device 28, associated with the incident point of the convergent electron beam on the evaluation sample, whereby the computed split width of the HOLZ line (lattice strain amount) and the incident point of the convergent electron beam can be associated with each other and can be displayed in a one-dimensional profile or a two-dimensional mapping.

FIG. 10 shows an example of the display of the evaluation result given by scanning one-dimensionally the channel region of a MOSFET in a channel-wise. FIG. 11 shows an example of display of the evaluation result given by two-dimensionally scanning the region of the silicon substrate below the contact plugs connected to the source/drain region of the MOSFET.

The stress measuring method according to the present embodiment cannot quantify the lattice strain amount but can give the correlation of the lattice strain amount among regions. Thus, the stress measuring method according to the present embodiment is useful to qualitatively evaluate regions to be evaluated.

As described above, according to the present embodiment, convergent electron beam is incident on an evaluation region of a crystalline material to be measured, a HOLZ pattern formed by the convergent electron beam which has been transmitted to the crystalline material is given, the split width of the HOLZ line is measured, based on the given HOLZ pattern, a lattice bending amount of the crystal material is evaluated, based on the measured spit width of the HOLZ line, whereby lattice strains in a disuniform strained site of much infinitesimal region can be qualitatively measured.

The stress measuring method and system according to the present embodiment is incorporated in the steps of fabricating, e.g., a silicon semiconductor device, and the measured results are fed back to the fabrication process, whereby the device structure can have lattice strains or stresses adjusted. Thus, the electronic device having characteristics as designed can be developed in shorter periods of time.

A Second Embodiment

The stress measuring method and system according to a second embodiment of the present invention will be explained with reference to FIGS. 12 to 13C. The same members of the present embodiment as those of the stress measuring method and system according to the first embodiment shown in FIGS. 1 to 11 are represented by the same reference numbers not to repeat or to simplify their explanation.

Figure 12:
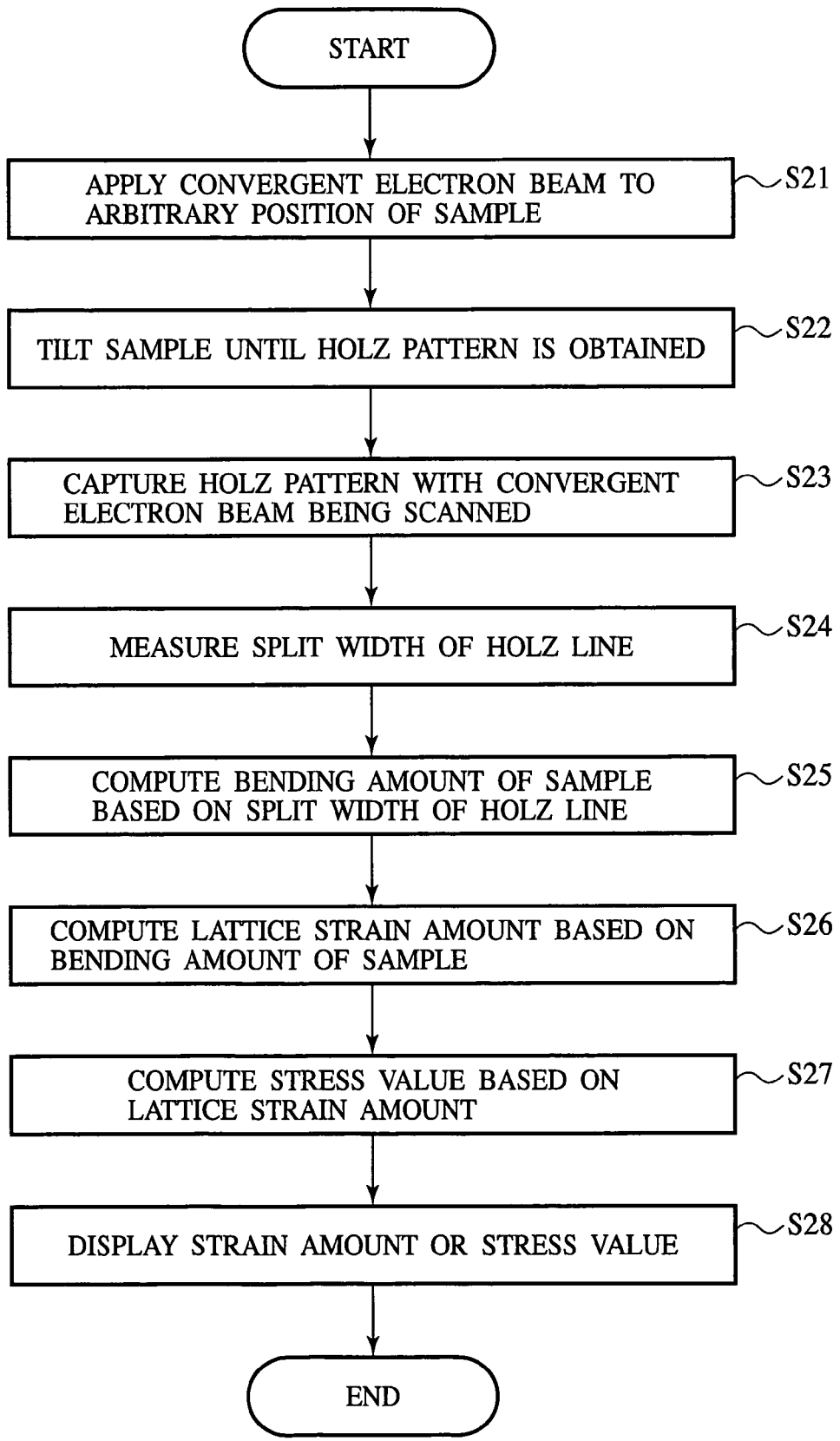
FIG. 12 is a flow chart of the stress measuring method according to a second embodiment of the present invention.
Figure 13A:
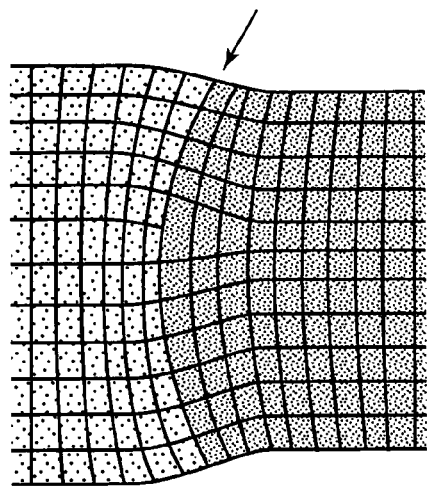
FIGS. 13A-13C are views showing a model used in computing the lattice strain amount, based on the lattice bending amount.
Figure 13B:
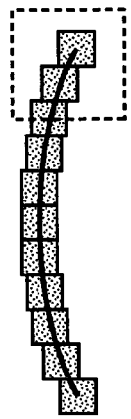
Figure 13C:
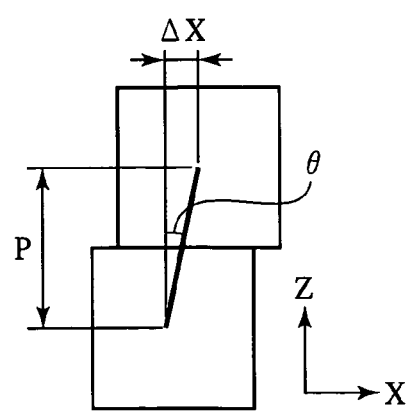

FIG. 12 is a flow chart of the stress measuring method according to the present embodiment. FIGS. 13A-13C are views showing a model used in computing the lattice strain amount, based on the lattice bending amount.

In the present embodiment, the stress measuring method which can quantify the lattice strain amount and the stress value in a region to be evaluated will be explained. The system used in the stress measuring method according to the present embodiment is the same as the stress measuring system according to the first embodiment.

FIG. 12 is a flow chart of the stress measuring method according to the present embodiment. In this flow chart, a HOLZ pattern in an evaluation region is measured (Steps S21-S23), a split width of the split HOLZ line is measured (Step S24), a lattice bending amount of the sample is computed, based on the split width of the HOLZ line (Step S25), the lattice strain amount is computed based on the lattice bending amount of the sample (Step S26), a stress value is computed based on the lattice strain amount (Step S27), and the computed lattice strain amount and/or the computed stress value are displayed (Step S28). The steps from Step S21 to Step S24 are the same as the Steps S11 to S14 of the stress measuring method according to the first embodiment.

First, in the same way as in the stress measuring method according to the first embodiment, with convergent electron beam being scanned, HOLZ pattern is captured, and based on the captured HOLZ pattern, the split width of the HOLZ line is measured (Step S21- Step S24).

Next, based on the computed spit width of the HOLZ line, the lattice bending amount of the sample is computed (Step S25).

As described above, the split width of a HOLZ line depends on a difference of the crystal orientation between the front surface of the sample and the back surface of the sample (=2θ). In other words, the split width of the HOLZ line is measured, whereby the angle θ can be computed as a parameter of the lattice bending amount of the sample.

When the measured split width of the HOLZ line is the same as those of the HOLZ pattern shown, e.g., in FIG. 9F, the crystal orientation difference between the sample front surface and the sample back surface, i.e., the lattice bending amount (2θ) can be computed to be, e.g., 3.06 [mrad]. The relationship between the split width of the HOLZ line and the lattice bending amount is in advance stored as the database in the outside memory device 28. Thus, the lattice bending amount of the sample can be immediately given, based on the computed split width of the HOLZ line.

Next, the strain amount of the crystal lattice is computed based on the lattice bending amount given based on the split width of the HOLZ line (Step S26).

It is assumed that the bent sample to be measured has eleven layers of single crystal (slices) stacked as shown in FIG. 13A. The thickness of the sample is 600 nm. The evaluation region is contained in the column indicated by the arrow in FIG. 13A.

FIG. 13B shows the column containing the evaluation region extracted from FIG. 13A. In FIG. 13B, the crystal orientation of the respective layers changes stage by stage, and the difference of the crystal orientation between the front surface of the sample and the back surface of the sample (=2θ) is computed to be, e.g., 3.06 [mrad], based on the measured split width of the HOLZ line. In the following description, for the convenience of the description, the tension and compression except those in the horizontal direction (X-direction) are ignored, and it is assumed that the strain has took place only in the horizontal direction.

The slice of the first layer and the slice of the second layer enclosed by the dotted line in FIG. 13B is noted. As shown in FIG. 13C, the shear amount ΔX in the X-direction between the slice of the first layer and the slice of the second layer is expressed by the following formula when a lattice bending amount is 2θ and a pitch (thickness) between the slices is p.

$$\tan\theta = \Delta X / p.$$

When the thickness of the sample is 600 nm, and a number of the thickness-wise slices is eleven, the pitch between the slices is 600/11=54.5 nm. Accordingly, the shear amount ΔX of the unit cell in the X-direction can be $$\Delta X = \tan(1.53 \ [mrad]) \times 54.5 = 8.338 \times 10^{-2} \ [nm].$$

When the evaluation sample is Si, because the lattice constant of Si is 0.54307 nm, the compression amount per the unit cell of the crystalline material in the X-direction is $$8.338 \times 10^{-2} \times 0.54307 / 54.5 = 8.308 \times 10^{-4} [nm].$$

Accordingly, the vertical strain amount $\epsilon_{xx}$ in the X-direction is $$\varepsilon_{xx} = 8.308 \times 10^{-4} / 0.54307 = 1.529 \times 10^{-3} \ [\%].$$

The strain amounts in the Y-direction and in the Z-direction can be also computed as described above.

Then, based on the crystal lattice strain amount given based on the lattice bending amount of the sample, value of a local stress applied to the crystal lattice is computed (Step S27).

The stress applied to the evaluation region is expressed by $$\begin{pmatrix} f_{xx} \\ f_{yy} \\ f_{zz} \end{pmatrix} = \begin{pmatrix} C_{11} & C_{12} & C_{12} \\ C_{12} & C_{11} & C_{12} \\ C_{12} & C_{12} & C_{11} \end{pmatrix} \begin{pmatrix} e_{xx} \\ e_{yy} \\ e_{zz} \end{pmatrix}$$

Here, $C_{11}$, and $C_{12}$ are elastic moduli, $e_{xx}$, $e_{yy}$ and $e_{zz}$ are lattice strain components respectively in the X-axial direction, the Y-axial direction and the Z-axial direction, and $f_{xx}$, $f_{yy}$ and $f_{zz}$ are stress components respectively in the X-axial direction, the Y-axial direction and the Z-axial direction.

The elastic moduli $C_{11}$, $C_{12}$ can be given based on the Young's modulus and the Poisson's ratio of a crystalline material to be measured. The lattice strain components $e_{xx}$, $e_{yy}$, $e_{zz}$ can be given in Step S26. The above-described formula is substituted with these values, and a local stress value applied to the evaluation region can be computed.

Then, the strain amount and/or the stress value in the evaluation region of the sample to be measured, which have been measured in the above-described steps are displayed on the display device (Step S28).

The processing from Step S25 to Step S27 is conducted on respective evaluation regions, and the incident points of the convergent electron beam on the sample, and the lattice strain amounts and/or the stress values at the respective incident points, which have been computed based on the HOLZ pattern can be stored in the outside memory device 28, associated with each other.

In Step S25, when the HOLZ pattern is given, the HOLZ pattern is stored in the outside memory device 28, associated with the ion incident points of the convergent electron beam on the sample to be measured, whereby the one-dimensional profile as shown in FIG. 10 and the two-dimensional profile as shown in FIG. 11 can be displayed, associated with the computed lattice strain amounts and/or the computed stress values. Especially in the stress measuring method according to the present embodiment, the lattice strain amount and the stress value can be quantitatively measured, which makes it possible to display the measured result together with quantified lattice strain amounts and stress values.

As described above, according to the present embodiment, convergent electron beam is incident on an evaluation region of a crystalline material to be measured, a HOLZ pattern formed by the convergent electron beam which has been transmitted to the crystalline material is given, the split width of the HOLZ line is measured based on the given HOLZ pattern, and a local lattice strain amount in the evaluation region is computed based on the measured spit width of the HOLZ line, whereby stress and lattice strain in a disuniformly strained site of much infinitesimal region can be precisely measured.

The stress measuring method and system according to the present embodiment is incorporated in the steps of fabricating, e.g., a silicon semiconductor device, and the measured results are fed back to the fabrication process, whereby the device structure can have lattice strains or stresses adjusted. Thus, the electronic device having characteristics as designed can be developed in shorter periods of time.

A Third Embodiment

The stress measuring method and system according to a third embodiment of the present invention will be explained with reference to FIGS. 14A to 20B. The same members of the present embodiment as those of the stress measuring method and system according to the first and the second embodiments shown in FIGS. 1 to 13 are represented by the same reference numbers not to repeat or to simplify their explanation.

Figure 14A:
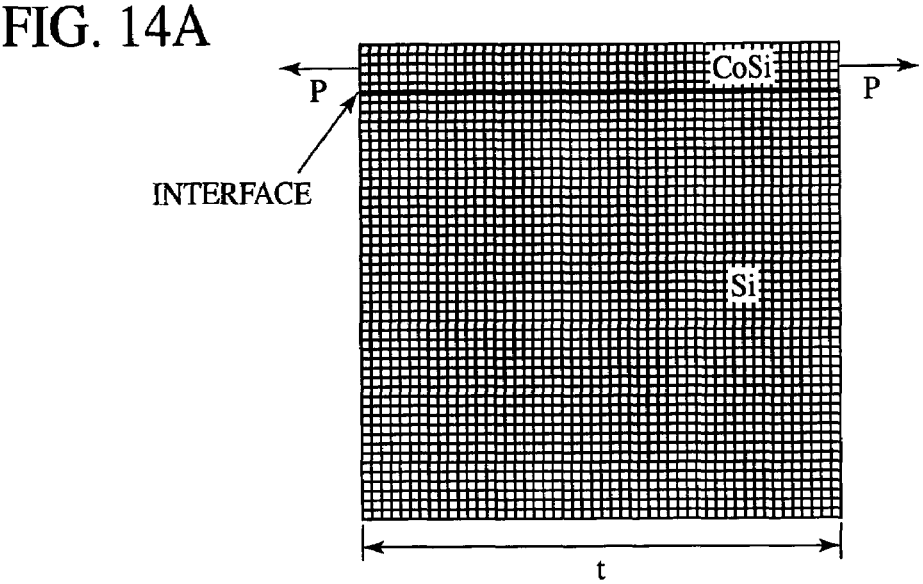
FIGS. 14A-14C are views showing a model used in computing the relationship between the distance from the interface with a stressor, and the lattice bending amount.
Figure 14B:
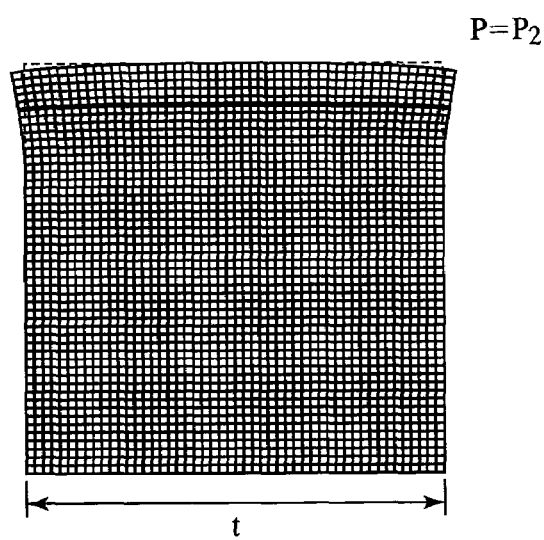
Figure 14C:
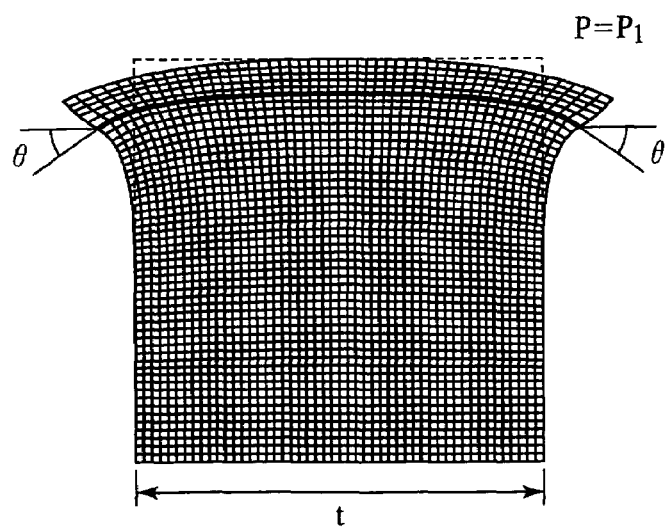
Figure 15:
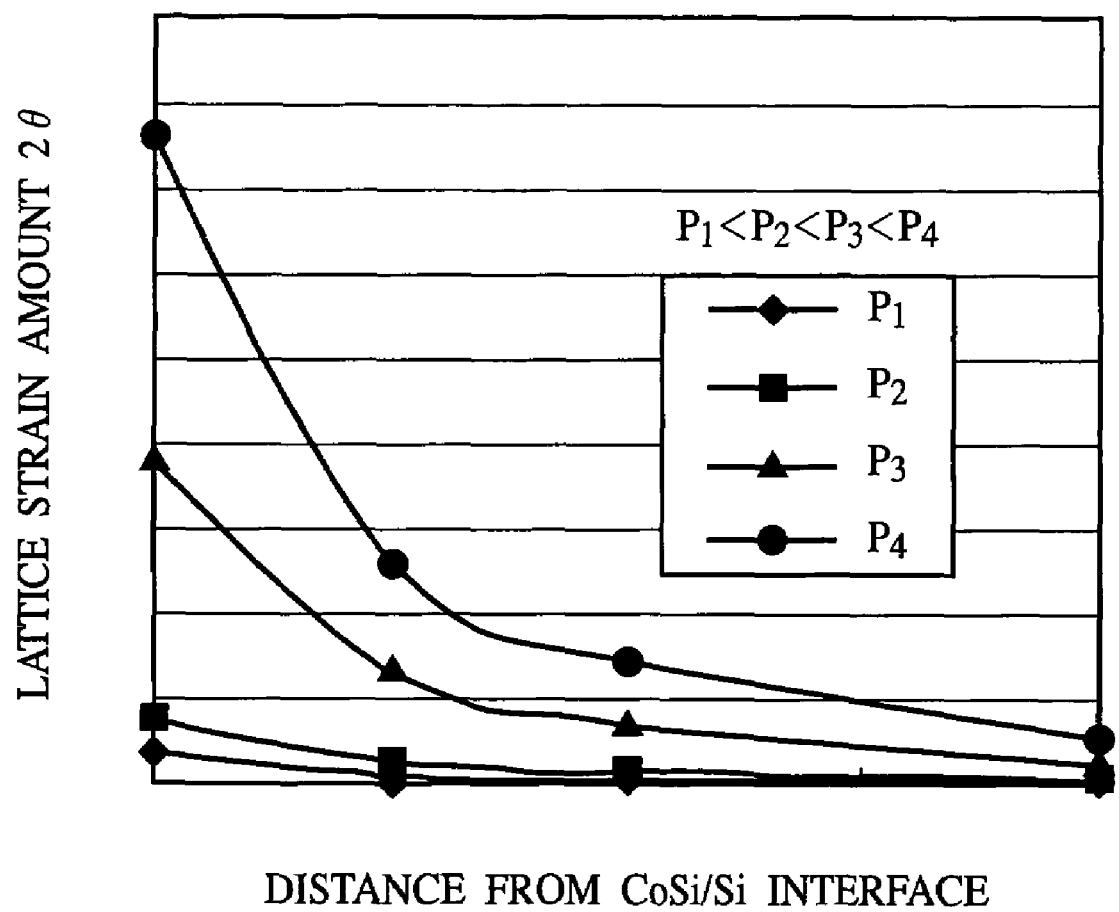
FIG. 15 is a graph showing the relationship between the distance from the interface with a stressor, and the lattice bending amount.
Figure 16:
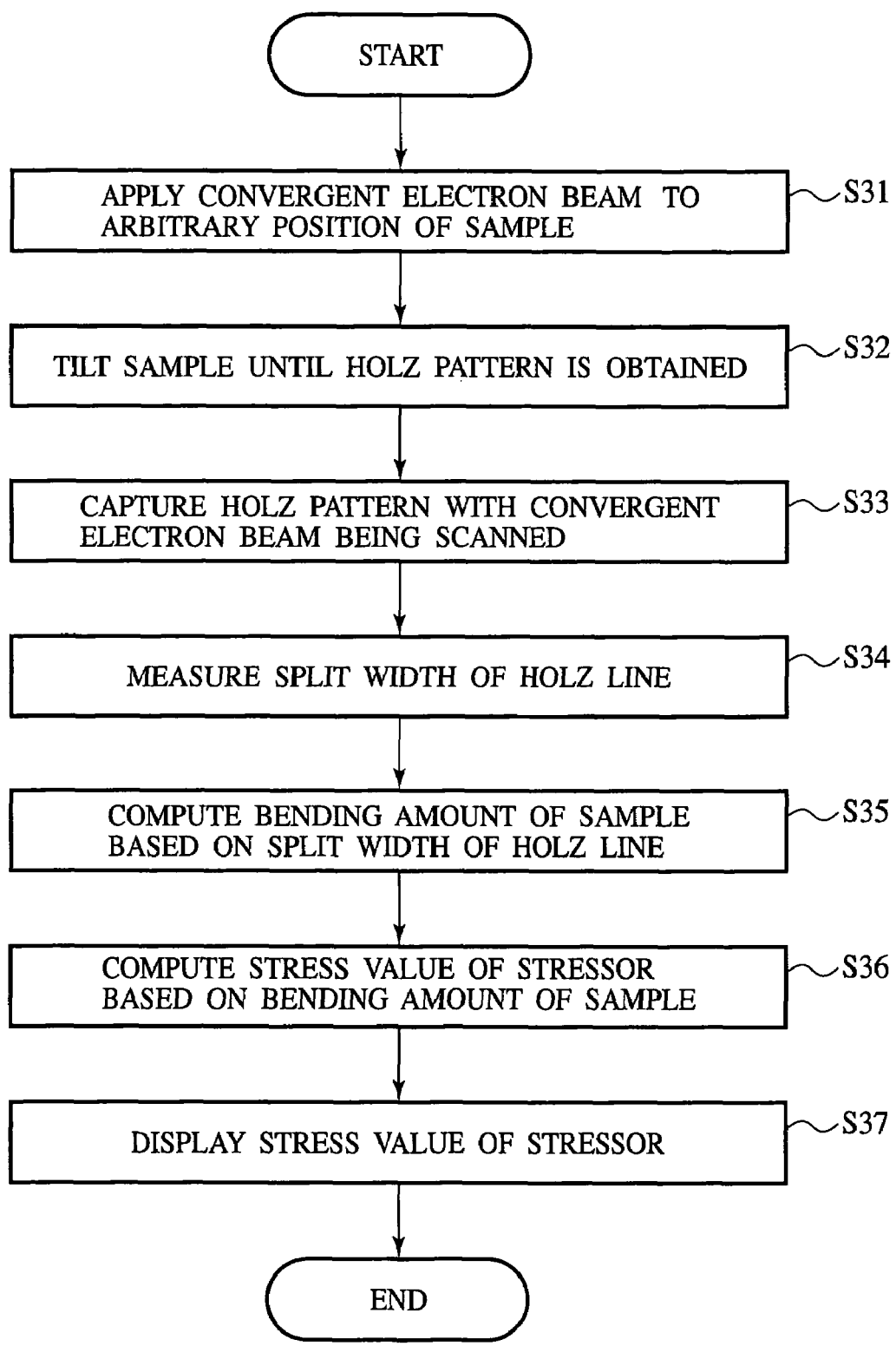
FIG. 16 is a flow chart of the stress measuring method according to a third embodiment of the present invention.
Figure 17:
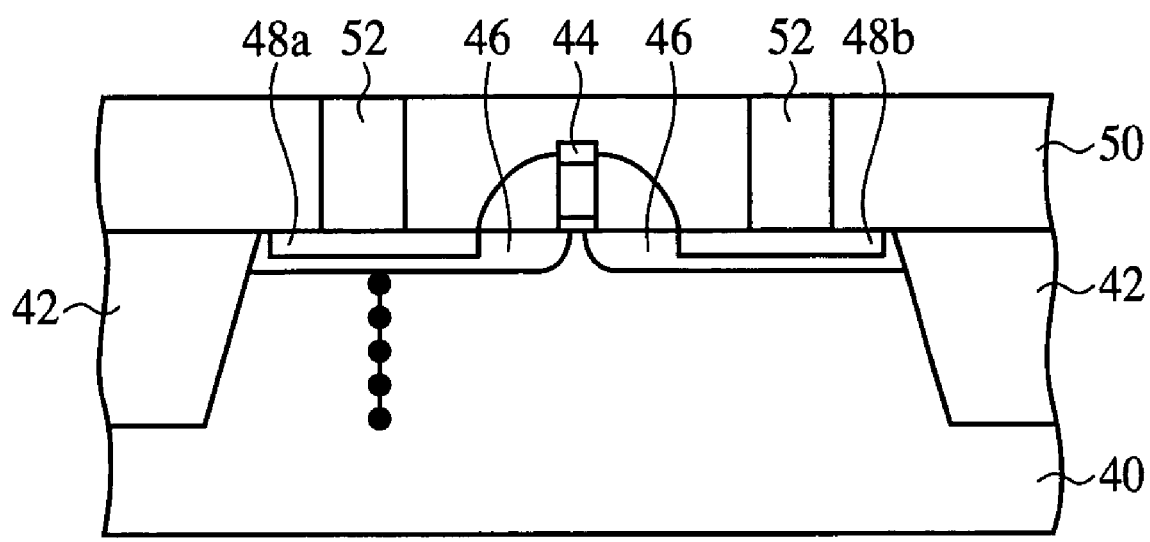
FIG. 17 is a diagrammatic sectional view showing one example of the sample to be measured and a region to be evaluated of the sample.
Figure 18:
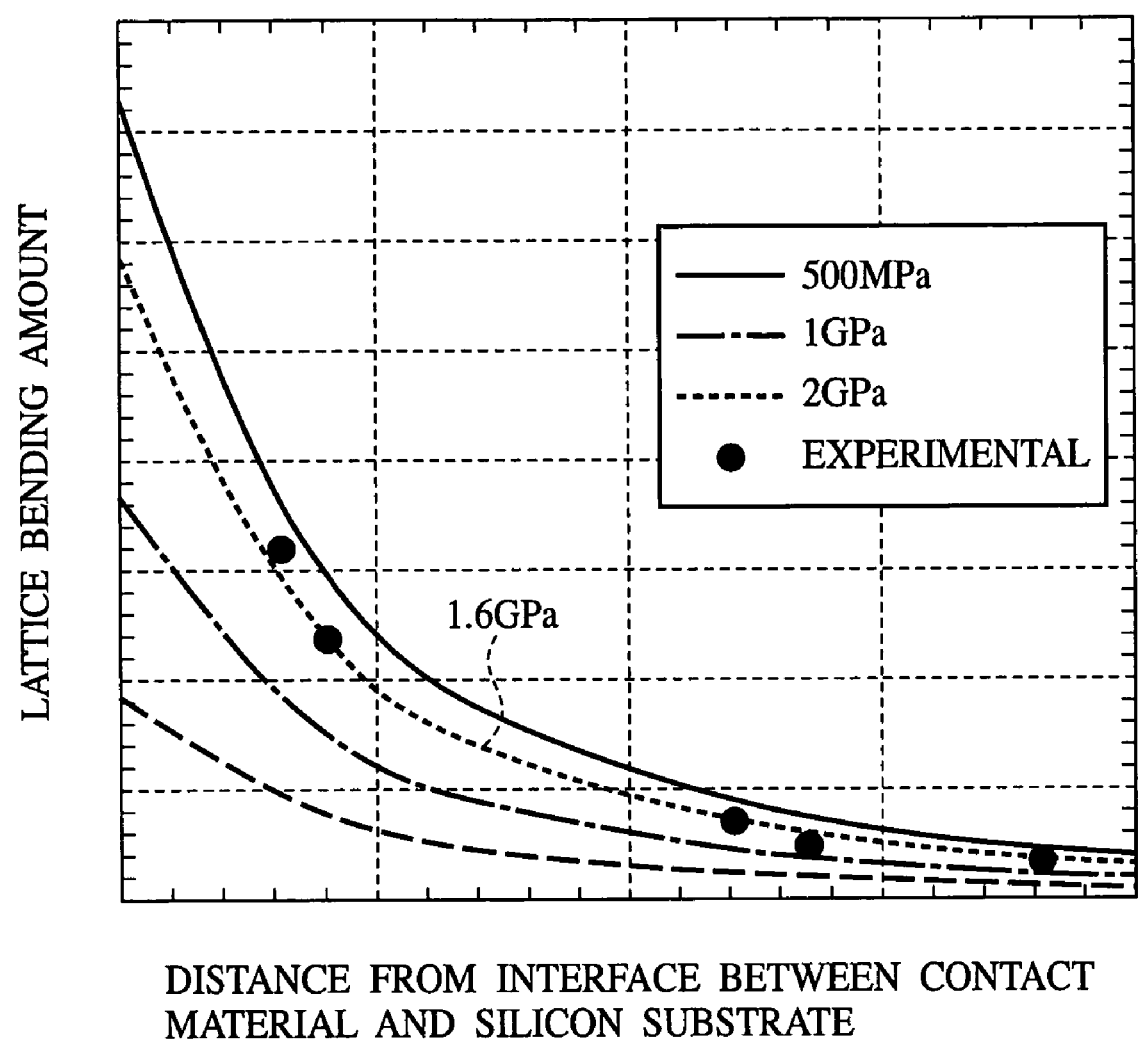
FIG. 18 is a graph showing the method for computing a stress value applied by the stressor, based on a measured value of the lattice-bending amount.

FIGS. 14A-14C are views showing a model used in computing the relationship between the distance from the interface with a stressor, and the lattice bending amount. FIG. 15 is a graph showing the relationship between the distance from the interface with a stressor, and the lattice bending amount. FIG. 16 is a flow chart of the stress measuring method according to the present embodiment. FIG. 17 is a diagrammatic sectional view showing one example of the sample to be measured. FIG. 18 is a graph showing the method for computing a stress value applied by the stressor, based on a measured value of the lattice bending amount. FIGS. 19A-19D are views showing the method for measuring a propagation direction of the stress from the stressor. FIGS. 20A and 20B are views showing the method for measuring a direction of a stress.

The stress measuring method according to the present embodiment can compute the stress value generated by a stress source. The system used in the stress measuring method according to the present embodiment is the same as that according to the first embodiment.

Before a sample is measured, the relationship between the distance from the interface with a stressor, and the lattice bending amount is computed by the finite-element method to give the database. The present embodiment will be explained by means of the case that a stress value applied by a cobalt silicide film formed on a silicon substrate to the silicon substrate is computed.

FIG. 14A is a view showing the model used in the computation by the finite-element method. In this model, it is assumed that a cobalt silicide (CoSi) film of a uniform thickness is formed on a silicon substrate (Si). The film thickness-wise direction of the same is horizontal to the drawing.

By using this model, bending contours of the sample are computed for various stress values of the cobalt silicide film. FIG. 14B shows the result of the lattice bending of the sample given by the finite-element method when the cobalt silicide film has a tensile stress $P_1$. FIG. 14C shows the result of the lattice bending to the sample given by the finite-element method when the tensile stress of the cobalt silicide film is $P_2$ which is larger than the tensile stress $P_1$.

For the respective computed sample contours, the lattice bending amounts are computed. The lattice bending amount is indicated by $2\theta$ with a difference of the crystal orientation on the sample surface caused by the application of a stress indicated by an angle $\theta$ (see FIG. 14C).

The lattice bending amount is computed with the distance from the interface between the cobalt silicide film and the silicon substrate as the parameter. Thus, as exemplified in FIG. 15, the relationship between the distance from the interface between the cobalt silicide film and the silicon substrate, and the lattice bending amount can be given.

As described above, the relationship between the distance from the interface with the stressor, and the lattice bending amount is given as the database and is stored in the outside memory device 28.

Next, following the flow chart of FIG. 16, a sample to be measured is measured. In this flow chart, a HOLZ pattern of an evaluation region is measured (Steps S31-S33), split width of the HOLZ line is measured (Step S34), a lattice bending amount of the sample is computed based on the split width of the HOLZ line (Step S35), a stress value of the stressor is computed based on the lattice bending amount (Step S36), and the stress value is displayed (Step S37). The steps from Step S31 to Step S35 are the same as Steps S21 to Step S25 of the stress measuring method according to the second embodiment.

First, in the same way as in the stress measuring method according to the second embodiment, a HOLZ patterns are captured with the convergent electron beam being scanned, the split width of the HOLZ line is measured based on the captured HOLZ pattern, and the lattice bending amount of the sample is computed based on the computed split width of the HOLZ line (Step S31 to Step S35).

In the present embodiment, it is assumed that the sample to be measured is the semiconductor device as exemplified in FIG. 17. A device isolation film 42 is formed on a silicon substrate 40. A MOSFET including a gate electrode 44 and source/drain regions 46 is formed in the device region defined by the device isolation film 42. A cobalt silicide film 48 is formed on the source/drain regions 46. An inter-layer insulating film 50 is formed on the silicon substrate 40 with the MOSFET formed on. Contact plugs 52 are buried in the inter-layer insulating film 50, connected to the cobalt silicide film 48.

The evaluation region is the silicon substrate 40 below the cobalt silicide film 48, and the measurement is made along the depth of the silicon substrate 40. In FIG. 17, the circles are measurement points, and the solid line interconnecting the circles is the scan path of the electron beam.

Next, the relationship between the distance from the interface with the stressor, and the computed lattice bending amount is compared with the database prepared beforehand, and a value of the stress applied by the stressor to the sample is computed (Step S36).

The database as exemplified in FIG. 18 is stored in the outside memory device 28. That is, in the database in the outside memory device 28, the relationship between the distance from the interface with the stressor, and the lattice bending amounts for stress values applied by the stressor of 500 MPa, 1 GPa and 2 GPa are stored.

In this case, when it is assumed that the measurement results indicated by the ● marks in FIG. 18 were given in measuring the real sample, these measurement points are compared with the stored relationship between the lattice bending amount and the distance from the interface with the stressor, whereby the value of the stress applied by the stressor in the real sample can be computed to be about 1.6 GPa.

Next, the stress value of the stress applied by the stressor, which has been computed in the above-described steps, is displayed on the display device 30 (Step S37).

The stress measurement based on the HOLZ pattern can not only quantify the stress value of a stress applied by the stressor, but also give a propagation direction of the stress and direction of the stress (tensile or compressive stress).

The propagation direction of the stress can be given based on the split direction of the HOLZ line. That is, the split direction of the HOLZ line agrees with the propagation direction of the stress, and the propagation direction of the stress can be given by giving the split direction of the HOLZ line.

Figure 19A:
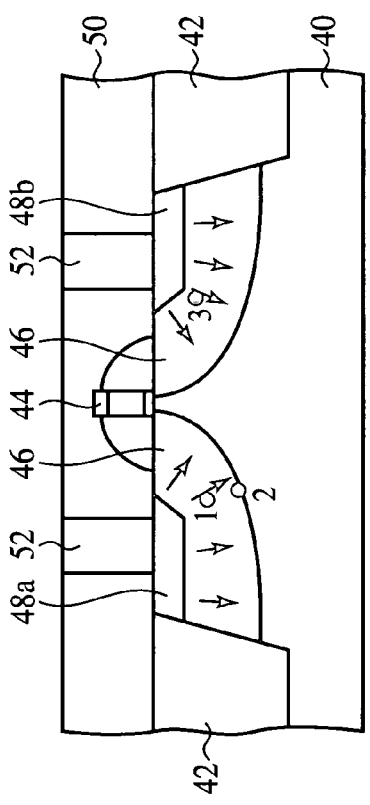
FIGS. 19A-19D are views showing the method for measuring a propagation direction of the stress from the stressor.
Figure 19D:
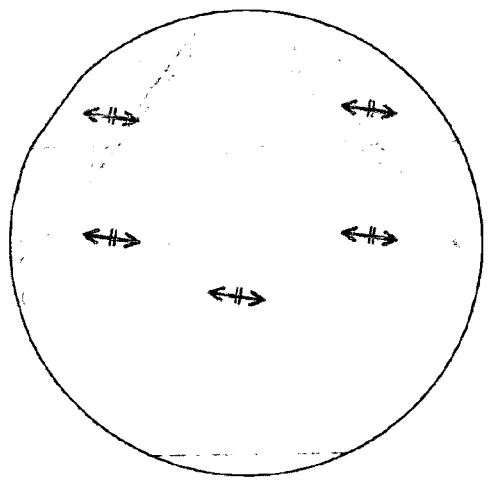
Figure 19C:
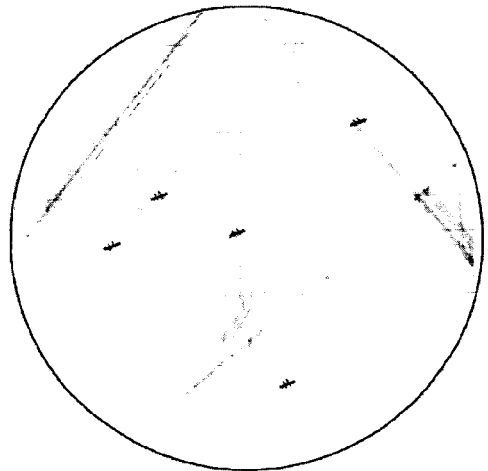
Figure 19B:
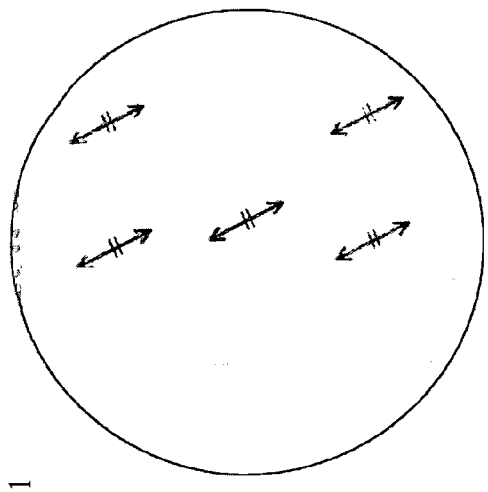
Figure 20A:
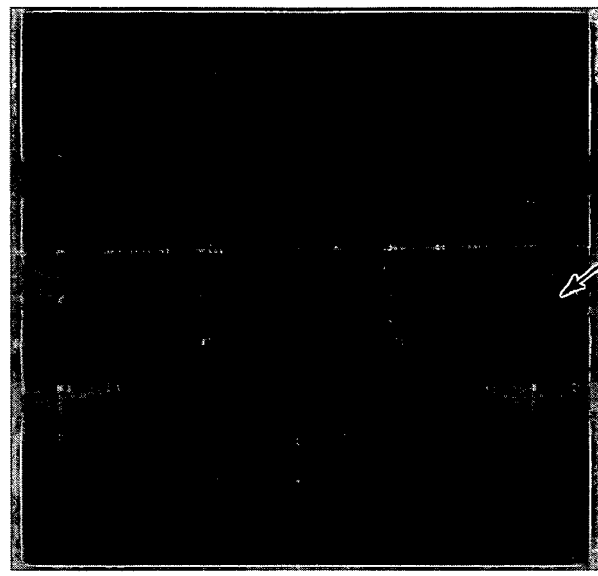
FIGS. 20A and 20B are views showing the method for measuring a direction of a stress.
Figure 20B:
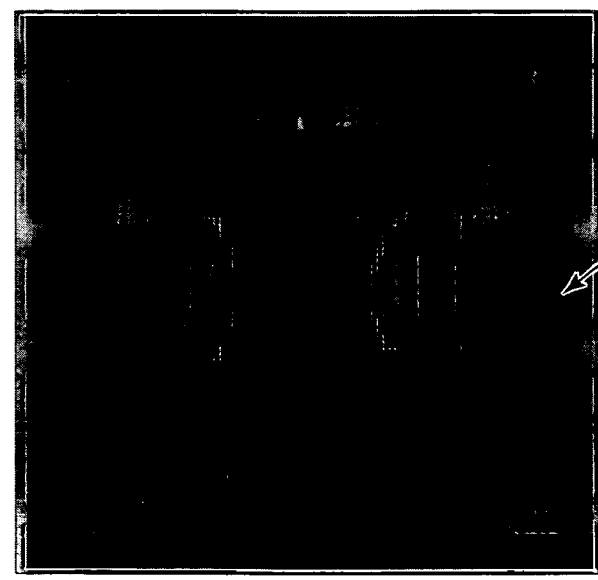

FIGS. 19A-19D are views showing the result of measuring the HOLZ pattern for the silicon substrate 40 with the MOSFET formed on. FIG. 19A shows a diagrammatic view of the sample to be measured, and FIGS. 19B, 19C and 19D show the HOLZ patterns measured for Region 1, Region 2 and Region 3, respectively.

As shown in FIGS. 19B and 19C, the split direction of the HOLZ line in Region 1 and Region 2 are slant upper left, and it is found that the stress propagates from the side of the cobalt silicide film 48*a*. It is also found that the lattice strain amount is smaller remoter from the cobalt silicide film 48*a*. As shown in FIG. 19D, the split direction of the HOLZ line in Region 3 is slant upper right, and it is found that the stress propagates from the side of the cobalt silicide film 48*b*.

The direction of a stress can be judged, based on the thickness of the sample. The thickness of the sample is increased when a tensile stress is applied to an evaluation region and decreases when a compressive stress is applied. The change amount of the thickness is larger nearer the interface with the stressor. Accordingly, the thickness of the sample in the evaluation region is compared with the thickness of the sample in a reference region which is less influenced by the stressor, whereby the direction of the stress applied to the evaluation region can be judged. The thickness of the sample can be judged, based on the convergent electron diffraction image.

FIGS. 20A and 20B show convergent electron diffraction images given when convergent electron beam is incident along the zone axis. In FIG. 20A, the thickness of the sample is 250 nm, and in FIG. 20B, the thickness of the sample is 275 nm.

As shown, when the thickness of the sample varies, the convergent electron diffraction image varies. In FIGS. 20A and 29B, the image especially in the part indicated by the arrow is changed. Accordingly, the thickness of the sample and the convergent electron diffraction image are given as the database, whereby, based on the convergent electron diffraction image, the thickness of the sample can be judged, and based on this, the direction of the stress can be judged.

As described above, according to the present embodiment, a convergent electron beam is incident on an evaluation region of a crystalline material to be measured, a HOLZ pattern formed by the convergent electron beam transmitted to the crystalline material is given, the split width of the HOLZ line of the given HOLZ pattern is measured, the lattice bending amount in the evaluation region is computed based on the measured split width of the HOLZ line, and the stress value of the stressor is computed based on the computed lattice bending amount and the distance from the stress source, whereby the stress applied to the crystalline material, the lattice strain, and also the stress value of the stress source applying the stress to the crystalline material can be precisely measured. The propagation direction of the stress from the stress source and the stress direction can be also judged.

The stress measuring method and system according to the present embodiment is incorporated in the steps of fabricating, e.g., a silicon semiconductor device, and the measured results are fed back to the fabrication process, whereby the device structure can have lattice strains or stresses adjusted. Thus, the electronic device having characteristics as designed can be developed in shorter periods of time.

Modified Embodiments

The present invention is not limited to the above-described embodiments and can cover other various modifications.

For example, in the above-described embodiments, the lattice bending amount in a silicon substrate with a MOSFET formed in, the stress values, etc. are measured. However, the stress measuring method according to the present invention is widely applied in measuring the lattice bending amount of disuniformly strained crystalline material, and the stress values.

In the above-described embodiments, the stressor which applies the stress to the evaluation region is cobalt silicide film. However, the stressor is not essentially cobalt silicide film.

What is claimed is:

1. A stress measuring method comprising:
    applying a convergent electron beam to an evaluation region of a crystalline material and obtaining a HOLZ pattern as a transmitted image of the convergent electron beam;
    measuring a split width of a HOLZ line of the HOLZ pattern; and
    evaluating a stress in the evaluation region of the crystalline material, based on the split width of the HOLZ line.

2. The stress measuring method according to claim 1, wherein
    a local lattice strain amount in the evaluation region of the crystalline material is computed based on the split width of the HOLZ line.

3. The stress measuring method according to claim 2, wherein
    the local lattice strain amount of the crystalline material is computed based on a split width of a HOLZ line computed by an electron diffraction computation using a model of a bent crystal lattice.

4. The stress measuring method according to claim 2, wherein
    a local stress value of a stress applied to the evaluation region of the crystalline material is computed based on the local lattice strain amount.

5. The stress measuring method according to claim 1, wherein
    a lattice bending amount of the crystalline material in the evaluation region is computed based on the split width of the HOLZ line, and
    based on a relationship between the lattice bending amount and a distance from a stress source to the evaluation region, a stress value of the stress source is computed.

6. The stress measuring method according to claim 5, wherein
    by a finite-element computation using a model in which a crystal lattice comprising two crystalline materials contact to each other is bent by applying a local stress, a relationship between a stress applied to the crystal lattice and a lattice bending amount of the crystal lattice is obtained,
    the relationship between the lattice bending amount and the distance from the stress source to the evaluation region computed based on the split width of the HOLZ line is compared with the relationship between the stress and the lattice bending amount of the crystal lattice computed by the model to thereby compute the stress value of the stress source.

7. The stress measuring method according to claim 1, wherein,
    a propagation direction of the stress in the evaluation region is judged based on a split direction of the HOLZ line.

8. The stress measuring method according to claim 1, wherein
    a direction of the stress is judged by comparing a thickness of the crystalline material in the evaluation region with a thickness of the crystalline material in a reference region.

9. The stress measuring method according to claim 8, wherein
    the thickness of the crystalline material is judged based on a convergent electron diffraction image given when the convergent electron beam is incident along a zone axis of the crystalline material.

10. The stress measuring method according to claim 1, wherein
    the convergent electron beam being incident on the crystalline material is scanned to thereby measure a distribution of the stress in a scanning region of the convergent electron beam.

11. A stress measuring system comprising:
    an electron microscope for applying a convergent electron beam to an evaluation region of a crystalline material and obtaining a HOLZ pattern given as a transmission image of the convergent electron beam; and
    a processing device for measuring a split width of a HOLZ line of the HOLZ pattern obtained by the electron microscope and evaluating a stress in the evaluation region of the crystalline material, based on the split width of the HOLZ line.

12. The stress measuring system according to claim 11, further comprising:
    a first database describing a relationship between the split width of the HOLZ line and a lattice bending amount of the crystalline material,
    the processing device comparing the measured split width of the HOLZ line with the first database to thereby compute a lattice bending amount of the crystalline material in the evaluation region, and computing a local lattice strain amount of the crystalline material in the evaluation region based on the lattice bending amount.

13. The stress measuring system according to claim 11, further comprising:
    a first database describing a relationship between the split width of the HOLZ line and a lattice bending amount of the crystalline material; and
    a second database describing a distance from a stress source applying the stress to the evaluation region, and the lattice bending amount of the crystalline material,
    the processing device comparing the measured split width of the HOLZ line with the first database to thereby compute the lattice bending amount of the crystalline material in the evaluation region, and comparing a relationship between the computed lattice bending amount and a distance from a stress source to the evaluation region with the second database to thereby compute a stress value of the stress source.

14. The stress measuring method according to claim 1, wherein
    a split of the HOLZ line of the HOLZ pattern is caused by a disuniform strain applied to the evaluation region.

* * * * *

UNITED STATES PATENT AND TRADEMARK OFFICE
CERTIFICATE OF CORRECTION

PATENT NO. : 7,342,226 B2  Page 1 of 2
APPLICATION NO. : 11/349131
DATED : March 11, 2008
INVENTOR(S) : Takeshi Soeda It is certified that error appears in the above-identified patent and that said Letters Patent is hereby corrected as shown below:

Drawings:
On Page 2 (Sheet 1 of 20):
Please delete "material reference figures 1A, 1B, 2A, 2B, 3A AND 3B" and reinstate original --FIGURE 1--.

Signed and Sealed this

Thirtieth Day of December, 2008

JON W. DUDAS
*Director of the United States Patent and Trademark Office*